US006235779B1

(12) United States Patent
Klimko et al.

(10) Patent No.: US 6,235,779 B1
(45) Date of Patent: May 22, 2001

(54) USE OF CIS-$\Delta^4$ ANALOGS OF PROSTAGLANDINS AS OCULAR HYPOTENSIVES

(75) Inventors: Peter G. Klimko; Paul W. Zinke, both of Fort Worth, TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/284,431

(22) PCT Filed: Nov. 7, 1997

(86) PCT No.: PCT/US97/20857

§ 371 Date: Jun. 2, 1999

§ 102(e) Date: Jun. 2, 1999

(87) PCT Pub. No.: WO98/21182

PCT Pub. Date: May 22, 1998

Related U.S. Application Data

(60) Provisional application No. 60/030,504, filed on Nov. 12, 1996.

(51) Int. Cl.$^7$ .................................................. A61K 31/215
(52) U.S. Cl. ......................... 514/530; 514/573; 514/912; 560/9; 562/427
(58) Field of Search .................................. 514/530, 573, 514/913; 560/9; 562/427

(56) References Cited

U.S. PATENT DOCUMENTS

| | | |
|---|---|---|
| 3,954,835 | 5/1976 | Samuelsson et al . |
| 4,032,561 | 6/1977 | Magerlein . |
| 4,065,628 | 12/1977 | Magerlein . |
| 4,065,629 | 12/1977 | Magerlein . |
| 4,138,574 | 2/1979 | Magerlein . |
| 4,212,985 | 7/1980 | Magerlein . |
| 4,241,215 | 12/1980 | Bowler . |
| 4,306,095 | 12/1981 | Bowler . |
| 4,599,353 | 7/1986 | Bito . |
| 5,001,153 | 3/1991 | Ueno et al. . |
| 5,321,128 | 6/1994 | Stjernschantz et al. . |
| 5,578,618 | 11/1996 | Stjernschantz et al. . |

FOREIGN PATENT DOCUMENTS

| | | |
|---|---|---|
| 0 299914 A1 | 1/1989 | (EP) . |
| O 561 073 A1 | 9/1993 | (EP) . |

OTHER PUBLICATIONS

Alm, The Potential of Prostaglandin Derivatives in Glaucoma Therapy, *Current Opinion in Ophthalmology*, 4 (11):44–50 (1993).

Bowler et al., Double Bond Isomers of Cloprostenol, *Prostaglandins*, 17(6):789–800 (1979).

Giuffre, The Effects of Prostaglandin $F_{2\alpha}$ the Human Eye, *Graefe's Archive Ophthalmology*, 222:139–141 (1985).

Green, Metabolism of $\Delta^4$–CIS–$PGF_{1\alpha}$ in the Monkey, *Prostaglandins* 15(5):813–821 (1978).

Green et. al., Decreased Rate of Metabolism Induced by a Shift of the Double Bond in Prostaglandin $F_{2\alpha}$ from the $\Delta^5$ to the $\Delta^4$ Position, *Eur. J. Biochem.*, 62:527–537 (1976).

Hansson, Metabolism of Two $PGF_{2\alpha}$ Analogues in Primates: 15(S)–15–Methyl–$\Delta^4$–CIS–$PGF_{1\alpha}$ And 16–16–Dimethyl–$\Delta^4$–CIS–$PGF_{1\alpha}$, *Prostaglandins*, 18(5):745–771 (1979).

Kerstetter et al., Prostaglandin $F_{2\alpha}$–1–Isopropylester Lowers Intraocular Pressure Without Decreasing Aqueous Humor Flow, *American Journal of Ophthalmology* 105:30–34 (1988).

Nakajima, Effects of Prostoglandin $D_2$ and its analogue, BW245C, on Intraocular Pressure in Humans, *Graefe's Archive Ophthalmology* 229:411–413 (1991).

Nidy and Johnson, Synthesis of 15–Methyl–cis–$\Delta^4$–Prostaglandins, *J. Org. Chem.*, 45(6):1121–1125 (1980).

Tarpley and Sun, Metabolism of cis–$\Delta^4$–15(S)–15–Methylprostaglandin $F_{1\alpha}$ Methyl Ester in the Rat, *J. Med. Chem.*, 21(3):288–291 (1978).

Thierauch, Prostaglandins and their Receptors: II. Receptor Structure and Signal Transduction, *Journal of Hypertension* 12:1–5 (1994).

*Primary Examiner*—Zohreh Fay
(74) *Attorney, Agent, or Firm*—Barry L. Copeland

(57) ABSTRACT

Cis-$\Delta^4$ analogs of prostaglandins and methods of their use in treating glaucoma and ocular hypertension are disclosed.

16 Claims, No Drawings

USE OF CIS-Δ⁴ ANALOGS OF PROSTAGLANDINS AS OCULAR HYPOTENSIVES

This Application claims the benefit of Provisional Application No. 60,030504 filed Nov. 12, 1996.

BACKGROUND OF THE INVENTION

The present invention relates to novel compounds for the treatment of glaucoma and ocular hypertension. In particular, the present invention relates to the use of certain cis-Δ⁴ analogs of D and F series prostaglandins to treat glaucoma and ocular hypertension.

Glaucoma is a progressive disease which leads to optic nerve damage, and, ultimately, total loss of vision. The causes of this disease have been the subject of extensive studies for many years, but are still not filly understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the flow of aqueous humor out of the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis, which side effects can affect patient compliance and/or necessitate the termination of treatment. Beta-blockers have increasingly become associated with serious pulmonary side effects attributable to their effects on beta-2 receptors in pulmonary tissue. Sympathomimetics may cause tachycardia, arrhythmia and hypertension. Recently, certain prostaglandins and prostaglandin derivatives have been described in the art as being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control elevated intraocular pressure associated with glaucoma without the degree of undesirable side-effects attendant to most conventional therapies.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-Series prostaglandins (EP 0 561 073 A1). Of interest in the present invention are compounds which are believed to exhibit IOP lowering mechanisms similar to those exhibited by $PGD_2$ (a D-series prostaglandin of formula I) and $PGF_{2\alpha}$ (an F-series prostaglandin of formula II):

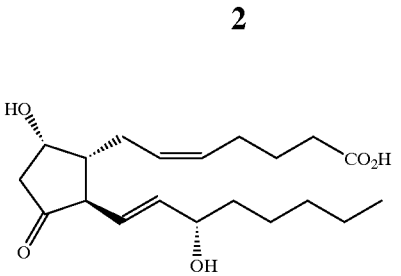

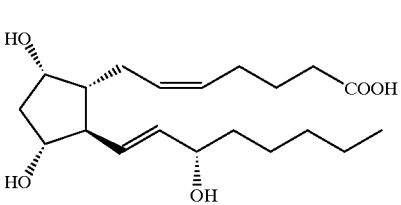

The relationship between $PGD_2$ receptor activation and IOP lowering effects is not well understood. Various publications have reported that $PGD_2$ receptor activation leads to second messenger activation and in particular, to the stimulation of adenylate cyclase and resultant increases in cAMP levels (Thierauch, *Prostaglandins and their Receptors: II. Receptor Structure and Signal Transduction*, Journal of Hypertension, volume 12, pages 1–5 (1994). Regardless of the mechanism, $PGD_2$ has been shown to lower IOP (Nakajima, *Effects of Prostaglandin $D_2$ and its analogue, BW245C, on Intraocular Pressure in Humans*, Graefe's Archive Ophthalmology, volume 229, pages 411–413 (1991)). Thus, it has been of interest in the ophthalmic field to develop synthetic $PGD_2$ analogs with IOP lowering efficacy.

Synthetic $PGD_2$-type analogs have been pursued in the art (*Graefe's Archive Ophthalmology*, volume 229, pages 411–413 (1991)). Though $PGD_2$-type molecules lower IOP, these types of molecules have also been associated with undesirable side effects resulting from topical ophthalmic dosing. Such effects have included an initial increase in IOP, conjuctival hyperemia, increases in microvascular permeability, and increases in eosinophile infiltration (Alm, *The Potential of Prostaglandin Derivatives in Glaucoma Therapy*, Current Opinion in Ophthalmology, volume 4, No. 11, pages 44–50 (1993)).

Similarly, the relationship of $PGF_{2\alpha}$ receptor activation and IOP lowering effects is not well understood. It is believed that $PGF_{2\alpha}$ receptor activation leads to increased outflow of aqueous humor. Regardless of the mechanism, $PGF_{2\alpha}$ and certain of its analogs have been shown to lower IOP (Giuffre, *The Effects of Prostaglandin $F_{2\alpha}$ the Human Eye*, Graefe's Archive Ophthalmology, volume 222, pages 139–141 (1985); and Kerstetter et al., *Prostaglandin $F_{2\alpha}$-1-Isopropylester Lowers Intraocular Pressure Without Decreasing Aqueous Humor Flow*, American Journal of Ophthalmology, volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology*, volume 229, pages 411–413 (1991)). Though $PGF_{2\alpha}$-type molecules lower IOP, a number of these types of molecules have also been associated with undesirable side effects resulting from topical ophthalmic dosing. Such effects include an initial increase in IOP, breakdown of the blood aqueous barrier and conjunctival hyperemia (Alm, *The Potential of Prostaglandin Derivatives in Glaucoma Therapy*, Current Opinion in Ophthalmology volume 4, No. 11, pages 44–50 (1993)).

Based on the foregoing, a need exists for the development of molecules that may activate the $PGD_2$ and/or $PGF_{2\alpha}$ receptors, yielding a more efficacious lowering of IOP, while exhibiting fewer or reduced side effects.

An agent which exhibits the same or improved efficacy, but with reduced side effects when compared to other agents, is said to have an improved therapeutic profile. It is an object of this invention to provide a class of IOP lowering agents with an improved therapeutic profile over their $PGF_{2\alpha}$ and $PGD_2$ counterparts, and methods of their use. It has now unexpectedly been discovered that the presently claimed cis-$\Delta^4$ analogs of $PGF_{2\alpha}$ and $PGD_2$ meet this objective. Certain cis-$\Delta^4$ analogs of $PGF_{2\alpha}$ (Nedy and Johnson, *J. Org. Chem.*, 45:6, 1121 (1980); Bowler et. al. *Prostaglandins*, 17:6, 789 (1979); DE 2,716,972; DE 2,637,384; DE 2,623, 139; U.S. Pat. No. 3,954,835) and $PGD_2$ (EPO 299,914 B1) are known in the art. The metabolic profiles of cis-$\Delta^4$ $PGF_{2\alpha}$ and (15S)-15-methyl-cis-$\Delta^4$ $PGF_{2\alpha}$ relative to the corresponding cis-$\Delta^5$ isomers have also been discussed in the art (Green et. al, *Eur. J. Biochem.*, 62, 527 (1976); Green, *Prostaglandins*, 15:5, 813 (1978); Hansson, *Prostaglandins*, 18:5, 745 (1979); Tarpley and Sun, *J. Med. Chem.*, 21:3, 288 (1978)). However, the surprisingly enhanced therapeutic profiles of such compounds and the novel compounds of the present invention in the treatment of glaucoma are neither disclosed nor suggested in that art.

SUMMARY OF THE INVENTION

The present invention is directed to compositions and methods of their use in treating IOP and ocular hypertension. In particular, the present invention provides certain classes of cis-$\Delta^4$ prostaglandin analogs, and methods of their use in treating glaucoma and ocular hypertension. As previously stated, the mechanism of action by which $PGD_2$ and $PGF_{2\alpha}$ type prostaglandins lower IOP is not well understood. Nevertheless, without being bound by any theories, the inventors postulate that the compounds of the present invention, with a cis double bond between carbons 4 and 5 in the alpha ($\alpha$) chain, are less susceptible to metabolic degradation than are their non-cis-$\Delta^4$ counterparts, and therefore enjoy a longer in vivo half-life than the non-cis-$\Delta^4$ compounds. A longer in vivo half life should enable relatively lower dosing and a reduction in side effects.

DETAILED DESCRIPTION OF THE INVENTION

It has unexpectedly been found that cis-$\Delta^4$ analogs of the present invention exhibit an improved therapeutic profile in the treatment of glaucoma and ocular hypertension when compared to natural prostaglandins and many of their known analogs. The cis-$\Delta^4$ analogs of the present invention are heptenoic acid derivatives having the following formula III:

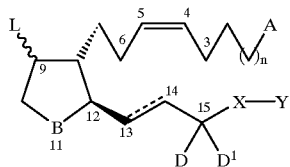

III wherein:
A=$CO_2R$, $CONR^1R^2$, $CH_2OR^3$, or $CH_2NR^4R^5$; where R=H or cationic salt moiety, or $CO_2R$= pharmaceutically acceptable ester moiety; $R^1$, $R^2$=same or different=H or alkyl; $R^3$=H, acyl, or alkyl; $R^4$, $R^5$=same or different=H, acyl, or alkyl, with the proviso that if one of $R^4$, $R^5$ =acyl, then the other=H or alkyl;

n=0 or 2;

L=$OR^6$ in the $\alpha$ configuration, where $R^6$=H, alkyl, or acyl; or L=halo in either configuration;

B=O,

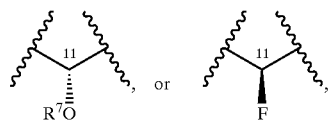

where $R^7$=H, alkyl, or acyl;

— — —=single or trans double bond;

D, $D^1$, taken together=$OCH_2CH_2O$; or D, $D^1$=different=H and $OR^8$, where $R^8$=H, alkyl, or acyl; or D=fluorine in the $\alpha$ configuration, and $D^1$=H in the $\beta$ configuration;

X=$(CH_2)_m$ or $(CH_2)_mO$, where m=1–6; and

Y=a phenyl ring optionally substituted with alkyl, halo, trihalomethyl, alkoxy, acyl, acyloxy, amino, alkylamino, acylamino, or hydroxy; or X—Y=$(CH_2)_pY^1$; where p=0–6; and

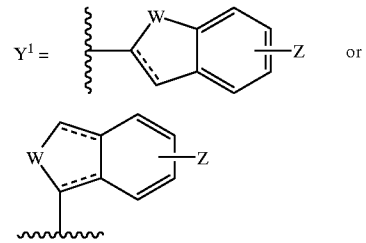

wherein:
W=$CH_2$, O, $S(O)_q$, $NR^9$, $CH_2CH_2$, CH=CH, $CH_2O$, $CH_2S(O)_q$, CH=N, or $CH_2NR^9$; where q=0–2, and $R^9$=H, alkyl, or acyl;

Z=H, alkyl, alkoxy, acyl, acyloxy, halo, trihalomethyl, amino, alkylamino, acylamino, or hydroxy; and — — —=single or double bond;

or X–Y=cyclohexyl;
with the proviso that the following compounds of formula III be excluded: those wherein: L=$OR^6$ in the $\alpha$ configuration, where $R^6$is as defined above;

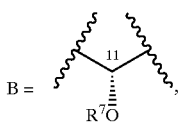

where $R^7$is as defined above;

— — —=trans double bond;

D, $D^1$=different=H and $OR^8$, where $R^8$ is as defined above;

X=$CH_2CH_2$ or $CH_2O$; and

Y=a phenyl ring, optionally substituted with halo.

For purposes of the foregoing and following definitions, the term "pharmaceutically acceptable ester" means any ester that would be suitable for therapeutic administration to a patient by any conventional means without significant deleterious health consequences; and "ophthalmically acceptable ester" means any pharmaceutically acceptable ester that would be suitable for ophthalmic application, i.e. non-toxic and non-irritating. Preferred are alkyl esters. Most preferred are $C_2$–$C_4$ alkyl esters, and especially isopropyl esters. For compounds of formula III where L=halo, preferred is chlorine in the β configuration.

Preferred for use in the methods and compositions of the present invention are those compounds of formula III above, wherein:

A=$CO_2R$, where R=H; or $CO_2R$=pharmaceutically acceptable ester moiety selected from the group consisting of ophthalmically acceptable ester moieties, where R=alkyl;

n=0;

L=OH in the α configuration;

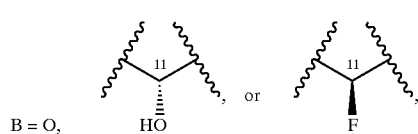

B = O,    or

D, $D^1$, taken together=$OCH_2CH_2O$; or D=OH in the α configuration, and $D^1$=H in the β configuration; or D=fluorine in the α configuration, and $D^1$=H in the β configuration;

X=$CH_2CH_2$ or $CH_2O$; and

Y=phenyl, optionally substituted with halo or trihalomethyl; or

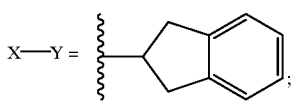

with the proviso that the following compounds of formula III be excluded, wherein:

A=$CO_2R$, where R=H or alkyl;

n=0;

L=OH in the α configuration;

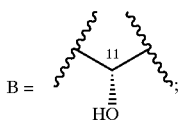

— — —=trans double bond;

D=OH in the α configuration, and $D^1$=H in the β configuration;

X=$CH_2CH_2$ or $CH_2O$; and

Y=a phenyl ring, optionally substituted with halo.

Especially preferred are the following compounds:

| Compound Number | Compound Name | Compound Structure |
|---|---|---|
| IV | (4Z,13E)-(9S,11R,15R)-16-(3-Trifluoromethylphenoxy)-9,11,15-trihydroxy-17,18,19,20-tetranor-4,13-prostadienoic acid isopropyl ester | 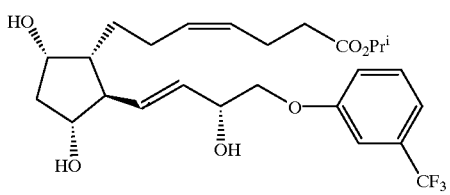 |
| V | (4Z,13E)-(9S,11R,15S)-15-(2-Indanyl)-9,11,15-trihydroxy-16,17,18,19,20-pentanor-4,13-prostadienoic acid isopropyl ester | 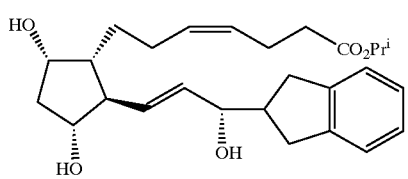 |
| VI | (4Z,13E)-(9S,11R)-16-(3-Chlorophenoxy)-9,11-dihydroxy-15-(1,3-dioxolan-2-yl)-17,18,19,20-tetranor-4,13-prostadienoic acid isopropyl ester | 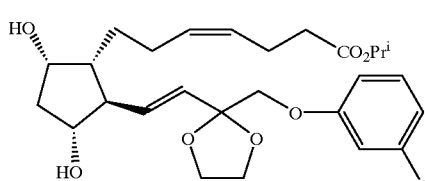 |

-continued

| Compound Number | Compound Name | Compound Structure |
|---|---|---|
| VII | (4Z,13E)-(9S,11S,15R)-9,15-Dihydroxy-11-fluoro-16-[(3-trifluoromethyl)phenoxy]-17,18,19,20-tetranor-4,13-prostadienoic acid isopropyl ester | 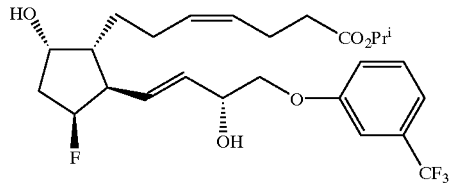 |
| VIII | Isopropyl[2R(1E,3R),3S(4Z),4R]-7-[Tetrahydro-2-[4-(3-chlorophenoxy)-3-hydroxy-1-butenyl]-4-hydroxy-3-furanyl]-4-heptenoate | 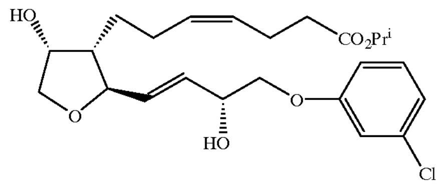 |
| IX | (4Z)-(9S,11R,15R)-16-(3-Chlorophenoxy)-9,11-dihydroxy-15-fluoro-17,18,19,20-tetranor-4-prostenoic acid isopropyl ester | 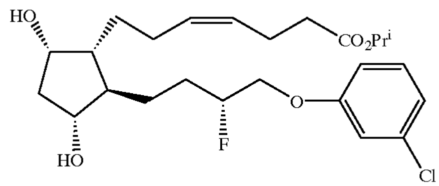 |

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis* by J. D. Morrison and J. W. Scott, Eds., Academic Press Publishers: New York, 1983–1985 (five volumes) and *Principles of Asymmetric Synthesis* by R. E. Gawley and J. Aube, Eds., Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*, G. Subramanian, Ed, VCH Publishers: New York, 1994; *Chiral Separations* by HPLC, A. M. Krstulovic, Ed., Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution or even mixing samples having different enantiomeric ratios.

Believed to be novel are compounds of formula III which contain a bicyclic aromatic group on the terminus of the ω chain, i.e., those wherein:

A=$CO_2R$, $CONR^1R^2$, $CH_2OR^3$, or $CH_2NR^4R^5$; where R=H or cationic salt moiety, or $CO_2R$ forms a pharmaceutically acceptable ester moiety; $R^1$, $R^2$=same or different=H or alkyl; $R^3$=H, acyl, or alkyl; $R^4$, $R^5$=same or different=H, acyl, or alkyl, with the proviso that if one of $R^4$, $R^5$ acyl, then the other=H or alkyl;

n=0 or 2;
L=$OR^6$ in the α configuration, where $R^6$=H, alkyl, or acyl;
B=O,

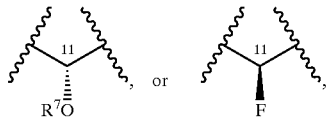

where $R^7$=H, alkyl, acyl;
— — —=single or trans double bond;
D, $D^1$, taken together=$OCH_2CH_2O$; or D, $D^1$=different=H and $OR^8$, where $R^8$=H, alkyl, acyl; or D=fluorine in the α configuration, and $D^1$=H in the β configuration;
X–Y=$(CH_2)_pY^1$; where p=0–6; and

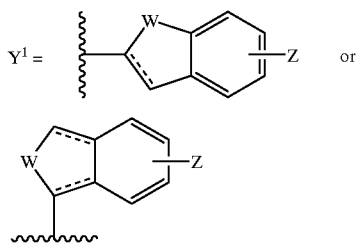

wherein:
W=$CH_2$, O, $S(O)_q$, $NR^9$, $CH_2CH_2$, CH=CH, $CH_2O$, $CH_2S(O)_q$, CH=N, or $CH_2NR^9$; where q=0–2, and $R^9$=H, alkyl, or acyl;
Z=H, alkyl, alkoxy, acyl, acyloxy, halo, trihalomethyl, amino, alkylamino, acylamino, or hydroxy; and
— — —=single or double bond.

Other related compounds within the scope of the present invention are known and their syntheses are either described in the literature or can be achieved by methods similar to those described in the literature or otherwise known to those of skill in the art. See, for example, *J. Org. Chem.*, 45:6, 1121 (1980); *Prostaglandins*, 17(6):789 (1979); *Eur. J. Biochem.*, 62:527 (1976); DE 2,826,462; DE 2,716,972; DE 2,623,139; EPO 299914 B1. The contents of these references are by this reference incorporated herein in their entirety.

In the foregoing illustrations, as well as those provided hereinafter, wavy line attachments indicate either the alpha (α) or beta (β) configuration. The carbon numbering is as indicated in structural formula III (even when n=2). A hatched line, as used e.g. at carbon 9, indicates the α configuration. A solid triangular line, as used e.g. at carbon 12, indicates the β configuration. Dashed lines on bonds, e.g. between carbons 13 and 14, indicate a single or double bond. Two solid lines between carbons indicate a double bond of the specified configuration.

In the following Examples 1–6, the following standard abbreviations are used: g=grams (mg=milligrams); mol= moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

Synthesis of IV

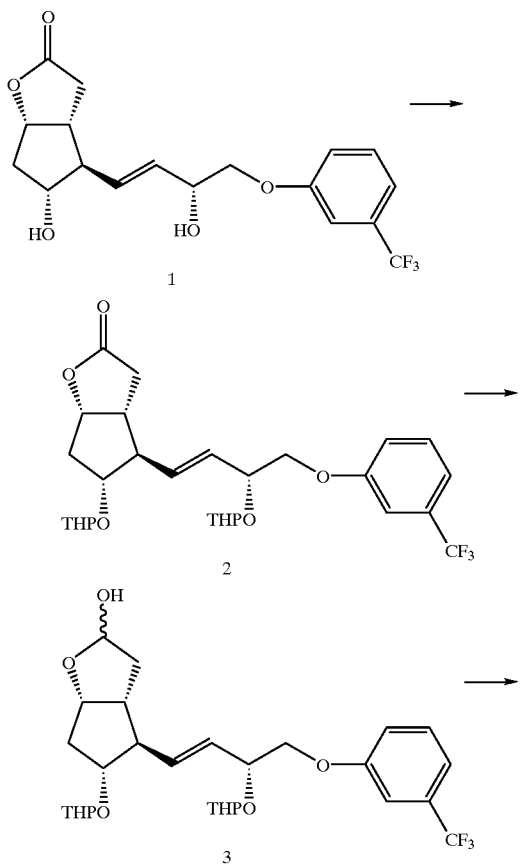

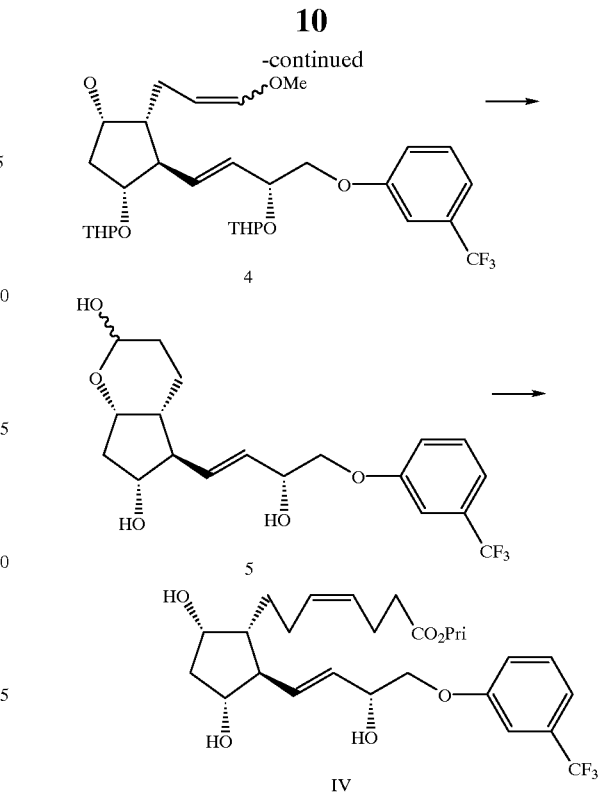

(4Z,13E)-(9S,11R,15R)-16-(3-Trifluoromethylphenoxy)-9,11,15-trihydroxy-17,18,19,20-tetranor-4,13-prostadienoic acid isopropyl ester (IV)

Reaction of diol 1 (for preparation, see U.S. Pat. No. 4,321,275, which is incorporated by this reference) with 3,4-dihydro-2H-pyran in CH$_2$Cl$_2$ at 0° C. in the presence of p-toluenesulfonic acid (TsOH) affords THP ether 2, which is reduced with diisobutylaluminum hydride (DIBAL-H) in toluene at −78° C. to afford lactol 3. Wittig reaction of 3 with Ph$_3$P$^+$CH$_2$OCH$_3$ Cl$^−$ in THF at 0° C. in the presence of potassium t-butoxide (KOBu$^t$) provides enol ether 4, which is hydrolyzed with TsOH in THF/water to yield lactol 5. Wittig reaction of 5 with Ph$_3$P$^+$(CH$_2$)$_3$CO$_2$H Br$^−$ in THF at 0° C. in the presence of KOBu$^t$, followed by alkylation of the product carboxylic acid with isopropyl iodide in acetone in the presence of DBU, yields IV after purification via silica gel chromatography.

EXAMPLE 2

Synthesis of V

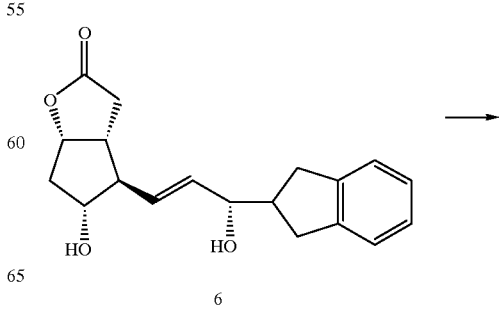

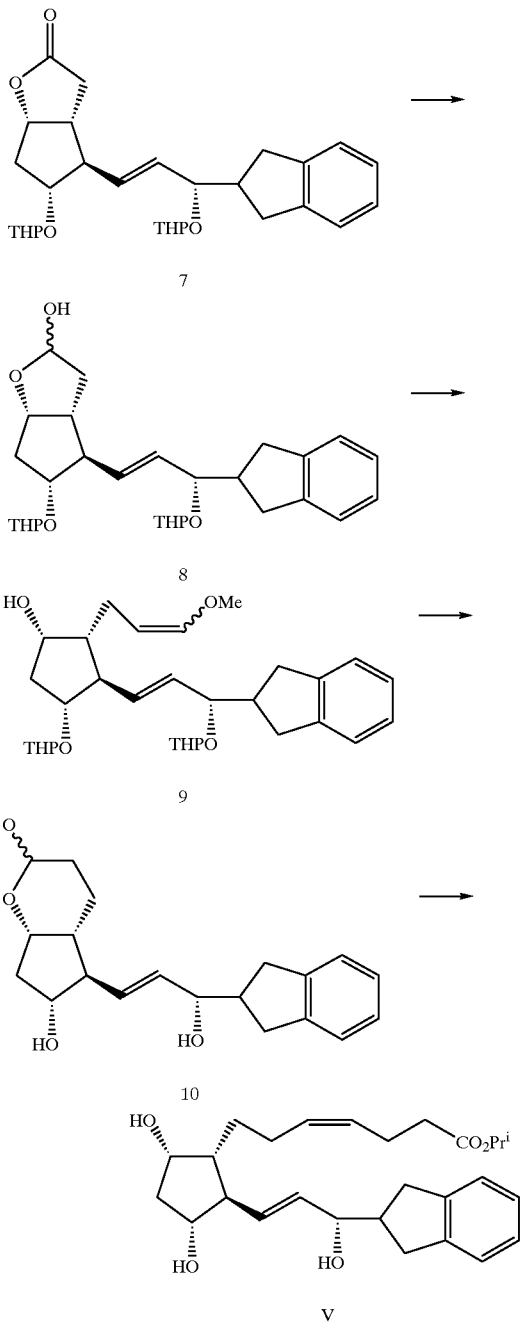

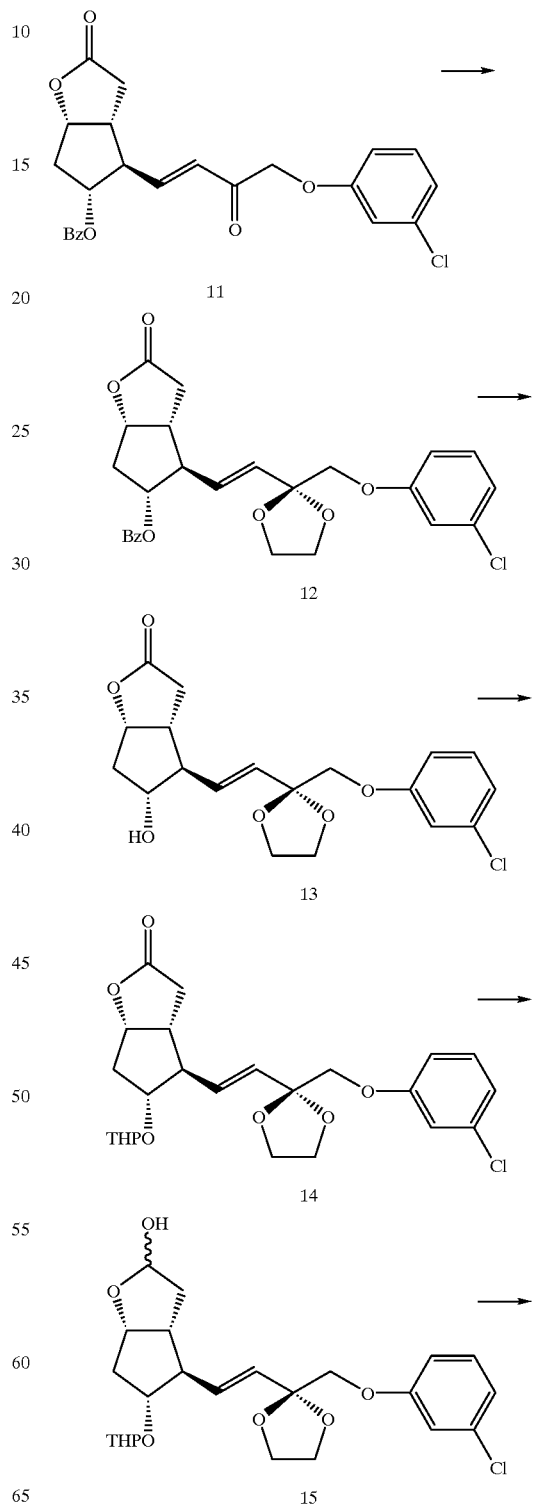

(4Z,13E)-(9S,11R,15S)-15-(2-Indanyl)-9,11,15-trihydroxy-16,17,18,19,20-pentanor-4,13-prostadienoic acid isopropyl ester (V)

Reaction of diol 6 (for preparation, see U.S. Pat. No. 4,152,527, which is incorporated by this reference) with 3,4-dihydro-2H-pyran in $CH_2Cl_2$ at 0° C. in the presence of TsOH affords THP ether 7, which is reduced with diisobutylaluminum hydride DIBAL-H in toluene at −78° C. to afford lactol 8. Wittig reaction of 8 with $Ph_3P^+CH_2OCH_3$ $Cl^-$ in THF at 0° C. in the presence $KOBu^t$ provides enol ether 9, which is hydrolyzed with TsOH in THF/water to yield lactol 10. Wittig reaction of 10 with $Ph_3P^+(CH_2)_3CO_2H$ $Br^-$ in THF at 0° C. in the presence of $KOBu^t$, followed by alkylation of the product carboxylic acid with isopropyl iodide in acetone in the presence of DBU, yields V after purification via silica gel chromatography.

EXAMPLE 3

Synthesis of VI

-continued

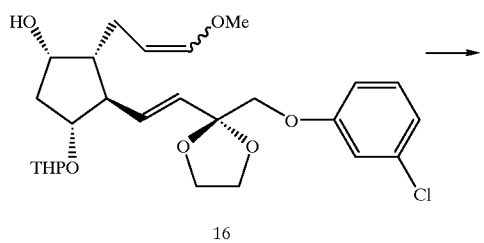

16

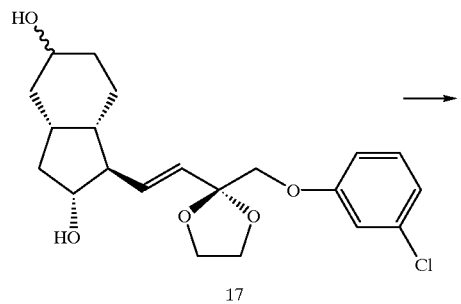

17

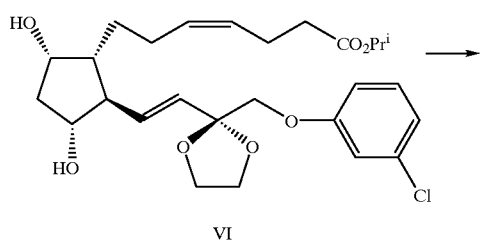

VI (4Z,13E)-(9S,11R)-16-(3-Chlorophenoxy)-9,11-dihydroxy-15-(1,3-dioxolan-2-yl)-17,18,19,20-tetranor-4,13-prostadienoic acid isopropyl ester (VI)

Ketalization of enone 11 (for preparation, see published European Patent Application No. EP 639563 A2, which is incorporated by this reference) with $(Me_3SiOCH_2)_2$ in $CH_2Cl_2$ at −78° C. in the presence of $Me_3SiOSO_2CF_3$ affords ketal 12, which is debenzoylated with potassium carbonate in methanol to provide alcohol 13. Reaction of 13 with 3,4-dihydro-2H-pyran in $CH_2Cl_2$ at 0° C. in the presence TsOH affords 14, reduction of which with DIBAL-H in toluene at −78° C. provides lactol 15. Wittig reaction of lactol 15 with $Ph_3P^+CH_2OMe\ Cl^-$ in the the presence of $KOBu^t$ in THF affords enol ether 16 as a mixture of enol ether olefin geometrical isomers. Treatment of this mixture with TsOH in THF/water affords lactol 17. Wittig reaction of 17 with $Ph_3P^+(CH_2)_3C_{O2}H\ Br^-$ in the presence of $KOBu^t$ in THF, followed by treatment of an acetone solution of the resulting carboxylic acid with DBU and isopropyl iodide, yields VI after purification via silica gel chromatography.

EXAMPLE 4

Synthesis of VII

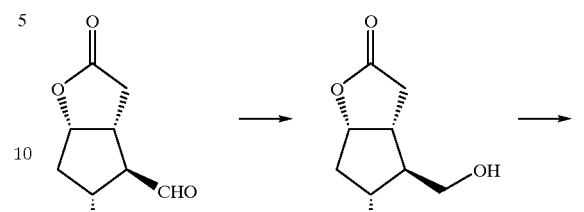

18    19

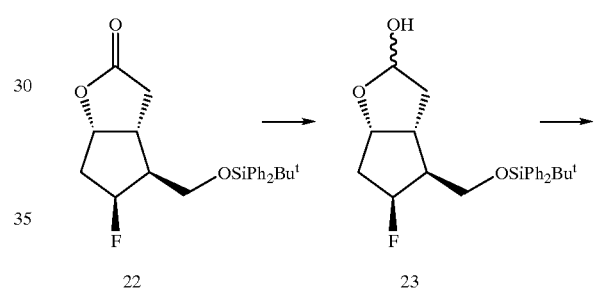

20    21

22    23

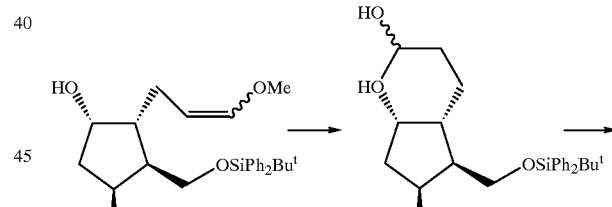

24    25

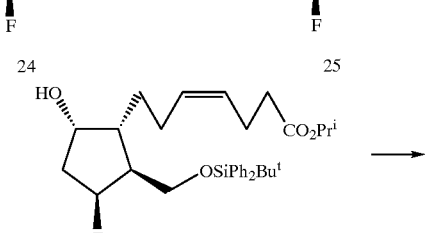

26

27

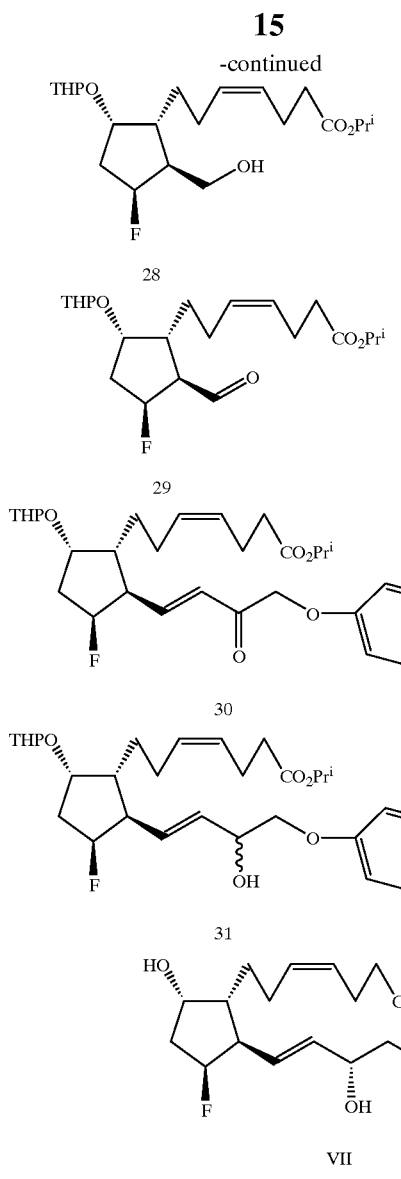

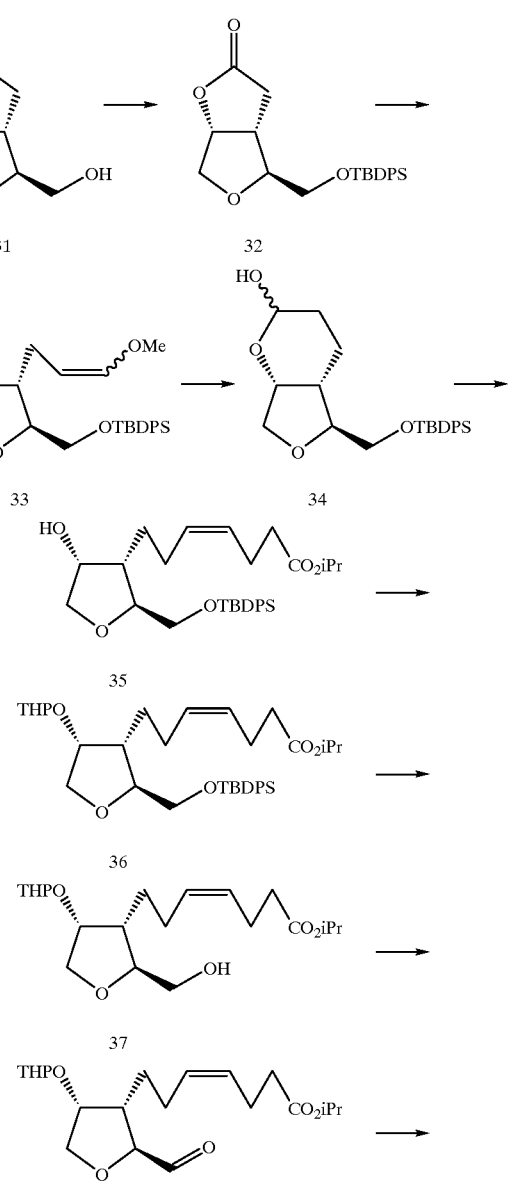

alkene 26. Treatment of 26 with 3,4-dihydro-2H-pyran in CH$_2$Cl$_2$ at 0° C. in the presence TsOH provides THP ether 27, which is desilylated using tetra-n-butylammonium fluoride in THF to give alcohol 28. Swern oxidation of 28 (oxalyl chloride, DMSO, CH$_2$Cl$_2$, NEt$_3$, −78° C.) affords aldehyde 29, which is treated with (MeO)$_2$P(O)CH$_2$C(O)CH$_2$OC$_6$H$_4$-m-CF$_3$, NEt$_3$, and LiCl in THF to provide enone 30. Luche reduction of 30 (NaBH$_4$, CeCl$_3$, MeOH, 0° C.) gives allyl alcohol 31 as a mixture of C-15 diastereomers. Acidic deprotection of 31 using aqueous HCl in isopropanol, followed by purification via silica gel chromatography, gives VII.

EXAMPLE 5

Synthesis of VIII (4Z,13)-(9S,11S,15R)-9,15-Dihydroxy-11-fluoro-16-[(3-trifluoromethyl)phenoxy]-17,18,19,20-tetranor-4,13-prostadienoic acid isopropyl ester (VII)

Reduction of aldehyde 18 with NaBH$_4$ in methanol/CH$_2$Cl$_2$ at 0° C. affords alcohol 19, which is treated with Ph$_2$Bu$^t$SiCl in CH$_2$Cl$_2$ in the presence of imidazole and 4-(dimethylaminopyridine to afford silyl ether 20. Debenzoylation is effected using potassium carbonate in methanol to provide alcohol 21, which is treated with (diethylamino) sulfur trifluoride (DAST) in CH$_2$Cl$_2$ at 0° C. After work-up and purification of the reaction via silica gel chromatography, the residue is stirred overnight with catalytic OsO$_4$ in acetone in the presence of stoichiometric N-methylmorpholine N-oxide to provide fluoride 22 after purification via silica gel chromatography. Reduction of 22 with DIBAL-H affords lactol 23, which is condensed with Ph$_3$P$^+$CH$_2$OMe Cl$^-$ in the the presence of KOBu$^t$ in THF to yield enol ether 24. Acidic hydrolysis using TsOH in THF/water gives lactol 25, which is reacted with Ph$_3$P$^+$(CH$_2$)$_3$CO$_2$H Br$^-$ in the presence of KOBu$^t$ in THF, followed by treatment of an acetone solution of the resulting carboxylic acid with DBU and isopropyl iodide, to afford

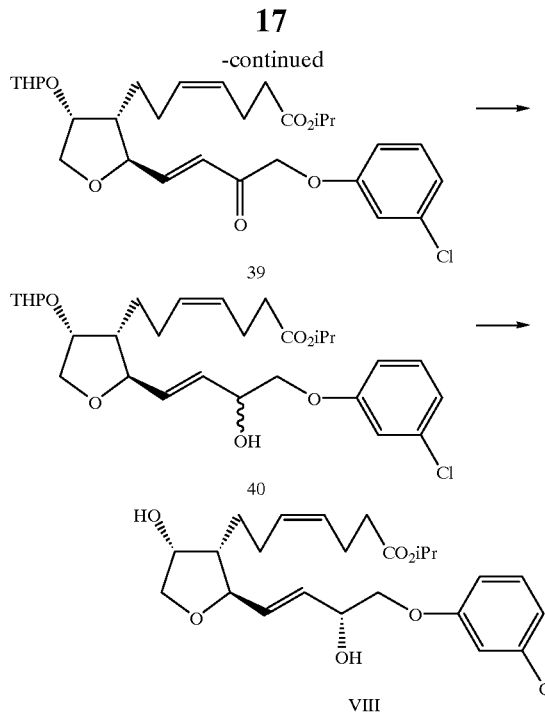

(3aR,4S,6aR)-4-(tert-Butyldiphenysilyloxy)methylhexahydrofuro[3,4-b]furan-2-one (32)

A mixture of alcohol 31 (for preparation, see U.S. Pat. No. 4,133,948, which is incorporated by this reference) (5.0 g, 31.6 mmol) and imidazole (4.3 g, 63.2 mmol) was dissolved in 100 mL of anhydrous DMF. To this solution tert-butyldiphenylsilyl chloride (10.4 g, 38.0 mmol) was added and the resulting mixture was stirred at room temperature for 14 h. The solvent was evaporated and the residue was taken up in 100 mL of EtOAc, washed with water (2×50 mL), dilute aqueous solution of HCl (2×50 mL) and brine and dried (MgSO4). The solvent was evaporated and the crude was purified by chromatography on silica gel to afford 32 (12.4 g, quantitative yield) as a white solid: $R_f$ 0.6 (60% EtOAc/hexanes). $^1$H-NMR (CDCl$_3$) δ 7.65 (m, 4H), 7.42 (m, 6H), 5.10 (m, 1H), 4.25 (dd, J=12, 4 Hz, 1H), 4.05 (dd, J=12, 2 Hz, 1H), 3.85 (m, 1H), 3.75 (m, 2H), 3.00 (m, 1H), 2.82 (dd, J=16, 7 Hz, 1H), 2.45 (dd, J=16, 2 Hz, 1H), 1.05 (s, 9H).

Isopropyl [2S,3 S(4Z),4R]-7-[Tetrahydro-2-(tert-butyldiphenylsilyloxy)methyl-4-hydroxy-3-furanyl]-4-heptenoate (35)

A solution of the lactone 32 (5.7 g, 14.5 mmol) in 150 mL of anhydrous THF was cooled to −78° C. under an inert atmosphere, and to it DIBAL-H (14.5 mL, 1.5 M in toluene, 21.7 mmol) was added dropwise. The resulting mixture was stirred at −78° C. for 1.5 h and was then quenched at the same temperature by the addition of 5 mL of methanol. The reaction was warmed to room temperature, an equal volume of a saturated aqueous solution of potassium sodium tartrate was added to it, and the resulting slurry was stirred at room temperature for 1 h. The layers were separated, and the aqueous layer was extracted with 3×25 mL of EtOAc. The organic layers were combined and washed with brine and dried (MgSO$_4$). The solution was filtered and concentrated and the crude was purified by passage through a short column of silica gel to afford the intermediate lactol (5.6 g, quantitative yield) as a colorless oil: $R_f$ 0.5 (60% EtOAc/hexanes).

A suspension of (methoxymethyl)triphenylphosphonium chloride (2.5 g, 7.5 mmol) in 70 mL of dry THF was cooled to 0° C. under a N$_2$ atmosphere. To this solution potassium tert-butoxide (t-BuOK, 9.0 mL, 1.0 M in THF, 9.0 mmol) was added dropwise, and stirring was continued at 0° C. for an additional 20 min. At this time a solution of the lactol obtained above (1.0 g, 2.5 mmol) in 30 mL of dry THF was added to it, and the resulting mixture was stirred at 0° C. for 1.5 h. The reaction was then worked up by pouring it into 50 mL of a saturated aqueous solution of KH$_2$PO$_4$, the layers were separated and aqueous layer was extracted with 3×25 mL of EtOAc. The combined organic layers were washed with water and brine, and dried (MgSO$_4$); solvent removal and chromatography of the crude on silica afforded the enolether 33 (0.89 g, 83% yield) as a colorless liquid: $R_f$ 0.6 (60% EtOAc/hexanes).

A solution containing enolether 33 (2.45 g, 5.7 mmol), p-toluenesulfonic acid (0.1 g) and water (10 mL) in 150 mL of THF was heated at reflux for 3 h. The mixture was then cooled to room temperature and poured into 50 mL of a saturated aqueous solution of NaHCO$_3$. The layers were separated and aqueous layer was extracted with EtOAc. The organic extracts were combined and dried (MgSO$_4$) and the crude product was subjected to chromatography on silica to afford 34 (1.44 g, 60% yield) as a colorless liquid. This material was used in the next reaction: $R_f$ 0.28 (50% EtOAc/hexanes).

A suspension of (3-carboxypropyl)triphenylphosphonium bromide (4.5 g, 10.5 mmol) in 70 mL of dry THF was cooled to 0° C. and to it t-BuOK (21.0 mL, 1.0 M in THF, 21.0 mmol) was added dropwise. The resulting solution was stirred for 30 min at 0° C. and to it a solution of the lactol 34 (1.44 g, 3.5 mmol) in 30 mL of dry THF was added dropwise over a period of 10 min. The reaction was allowed to warm to room temperature gradually, and was stirred at that temperature for 14 h. The mixture was then poured into 50 mL of a saturated aqueous solution of KH$_2$PO$_4$, and extracted with 3×25 mL of EtOAc. The organic extracts were combined and washed with brine, and dried (MgSO4). Filtration and solvent removal afforded an oily residue which was used immediately in the subsequent step.

The crude product from above was dissolved in 40 mL of acetone and the solution was treated with DBU (12.0 mL, 84 mmol) at room temperature for 10 min. Isopropyl iodide (7.0 mL, 70 mmol) was then introduced and the resulting mixture was stirred at room temperature for 18 h. Solvent was evaporated, and the residue was dissolved in 50 mL of EtOAc. This solution was washed sequentially with 3×25 mL of a saturated aqueous solution of KH$_2$PO$_4$, 1×10 mL of water and brine and dried over anhydrous MgSO$_4$. Filtration, solvent removal and chromatography of the crude on silica gel afforded the desired isopropyl ester 35 (1.18 g, 65% yield from 34) as a slightly yellow liquid: $R_f$ 0.2 (30% EtOAc/hexanes); $^1$H-NMR (CDCl$_3$) δ 7.71 (m, 4H), 7.40 (m, 6H), 5.38 (m, 2H), 5.00 (septet, J=6.4 Hz, 1H), 4.38 (m, 1H), 3.65–4.00 (broad m, 5H), 1.90–2.50 (broad m, 7H), 1.55 (m, 2H), 1.23 (d, J 7.2 Hz, 6H), 1.05 (s, 9H); MS m/z at 547 for (M+Na)$^+$.

Isopropyl [2S,3R(4Z),4R]-7-[Tetrahydro-2-hydroxymethyl-4-(tetrahydropyran-2-yl)oxy-3-furanyl]-4-heptenoate (37)

A solution of the alcohol 35 (1.18 g, 2.3 mmol) and 3,4-dihydro-2H-pyran (0.3 mL, 3.4 mmol) in 50 mL of CH$_2$Cl$_2$ was cooled to 0° C. and to it a catalytic amount of p-toluenesulfonic acid (10 mg) was added. The resulting mixture was stirred at 0° C. for 25 min and was then quenched by the addition of 25 mL of a saturated aqueous solution of NaHCO$_3$. The mixture was warmed to room temperature, the layers were separated and the aqueous layer was extracted with 3×25 mL of CH$_2$Cl$_2$. The organic layers were combined and washed with brine and dried ($K_2CO_3$). The crude obtained after filtration and solvent removal was purified by passage through a short plug of silica to afford the intermediate tetrahydropyranyl ether 36 as colorless liquid: $R_f$ 0.4 (30% EtOAc/hexanes).

The silyl ether 36 thus obtained was dissolved in 20 mL of THF and the solution was treated with tetra-n-butylammonium fluoride (7.0 mL, 1.0 M in THF, 7.0 mmol) at room temperature for 2 h. The reaction mixture was then poured into water and was extracted with EtOAc (3×25 mL). The organic extracts were combined and dried (MgSO4), filtered and concentrated. The crude was subjected to chromatography on silica to afford the alcohol 37 (0.72 g, 85% yield from 35) as a colorless liquid: $R_f$ 0.16 (50% EtOAc/hexanes); $^1$H-NMR ($d_6$-DMSO) δ (partial spectrum) 5.36 (m, 2H), 4.87 (septet, J=6.5 Hz, 1H), 4.60 (m, 2H), 1.18 (d, J=7.2 Hz, 6H).

Isopropyl [2S,3R(4Z),4R]-7-[Tetrahydro-2-formyl-4-(tetrahydropyran-2-yl)oxy-3-furanyl]-4-heptenoate (38)

A solution of oxalyl chloride (2.0 mL, 2.0 M in $CH_2Cl_2$, 4.0 mmol) in 10 mL of dry $CH_2Cl_2$ was cooled to −78° C., and to it a solution of DMSO (0.56 mL, 8.0 mmol) in 5 mL of $CH_2Cl_2$ was introduced dropwise. After the mixture was stirred for 3 min at −78° C., a solution of the substrate 37 (0.72 g, 2.0 mmol) in 25 mL of $CH_2Cl_2$ was added to it dropwise. The mixture was stirred for 15 min, at which time triethylamine (1.7 mL, 12.0 mmol) was introduced, and stirring was continued for an additional 15 min. The reaction was gradually warmed to room temperature and then poured into 50 mL of water. The layers were separated and the water layer was extracted with 3×25 mL of $CH_2Cl_2$. The combined organic extracts were washed with water and brine, and dried ($MgSO_4$). Filtration and solvent removal, followed by chromatography of the crude on silica afforded the aldehyde 38 (0.69 g, 94% yield) as a pale yellow liquid: $R_f$ 0.3 (50% EtOAc/hexanes); $^1$H-NMR (CDCl$_3$) δ (partial spectrum) 9.66 (d, J=3 Hz, 1H), 5.37 (m, 2H), 5.0 (septet, J=6.5 Hz, 1H), 1.24 (d, J=7.2 Hz, 6H).

Isopropyl [2R(1E),3R(4Z),4R]-7-[Tetrahydro-2-[4-(3-chlorophenoxy)-3-oxo-1-butenyl]-4-(tetrahydropyran-2-yl)oxy-3-furanyl]-4-heptanoate (39)

A mixture of the aldehyde 38 (0.32 g, 0.87 mmol), dimethyl-3-(3-chlorophenoxy)-2-oxopropylphosphonate (1.0 g, 3.5 mmol) and LiCl (0.15 g, 3.5 mmol) was taken up in 40 mL of dry THF, and the solution was cooled to 0° C. under a $N_2$ atmosphere. To this solution triethylamine (0.5 mL, 3.5 mmol) was added dropwise, and the resulting slurry was stirred at 0° C. for 1 h. The reaction was then quenched by pouring it into 50 mL of a saturated aqueous solution of $KH_2PO_4$. The organic layer was separated and the aqueous layer was extracted with 3×25 mL of EtOAc. The organic extracts were combined and washed with water and brine and dried ($MgSO_4$). The crude product mixture was subjected to chromatography on silica to afford the enone 39 (0.34 g, 73% yield) as a pale yellow liquid: $R_f$ 0.6 (60% EtOAc/hexanes); $^1$H-NMR (CDCl$_3$) δ (partial spectrum) 6.70–7.20 (broad m, 5H), 6.12 (d, J=16.7 Hz, 1H), 5.36 (m, 2H), 5.0 (septet, J=6.5 Hz, 1H), 4.73 (s, 2H), 1.23 (d, J=7.5 Hz, 6H).

Isopropyl [2R(11E,3RS),3R(4Z),4R]-7-[Tetrahydro-2-[4-(3-chlorophenoxy)-3-hydroxy-1-butenyl]-4-(tetrahydropyran-2-yl)oxy-3-furanyl]-4-heptenoate (40)

A mixture of the enone 39 (0.34 g, 0.64 mmol) and $CeCl_3 \cdot 7H_2O$ (0.47 g, 1.27 mmol) was dissolved in 30 mL of methanol and the solution was cooled to −5° C. NaBH$_4$ (47 mg, 1.27 mmol) was added to the solution in small portions over a period of 3 min. The mixture was stirred for an additional 3 min and the reaction was then quenched at −5° C. by the addition of 10 mL of a saturated aqueous solution of $NH_4Cl$. The resulting slurry was warmed to room temperature and partitioned between $CHCl_3$ and water. The aqueous layer was extracted with 3×25 mL of $CHCl_3$ and the combined organic extracts were washed with 2×10 mL of water and brine. The organic layer was dried, filtered and concentrated and the crude was purified by chromatography on silica to afford the reduction product 40 (0.30 g, 87% yield) as a colorless liquid: $R_f$ 0.24 (50% EtOAc/hexanes).

Isopropyl [2R(1E,3R),3S(4Z),4R]-7-[Tetrahydro-2-[4(3-chlorophenoxy)-3-hydroxy-1-butenyl]-4-hydroxy-3-furanyl]-4-heptenoate (VIII)

The allyl alcohol 40 (0.30 g, 0.55 mmol) was dissolved in a mixture of 10 mL of methanol and 1.0 mL of water, and the solution was cooled to 0° C. Approximately 10 drops of 12 N HCl was added to it dropwise, and stirring was continued at 0° C. for 15 min and then at room temperature for 1 h. The reaction was then quenched by the addition of solid $NaHCO_3$, and the suspension was partitioned between $CHCl_3$ and water. The layers were separated and the aqueous layer was extracted with 3×25 mL of $CHCl_3$. The organic extracts were combined and washed with water (2×10 mL) and brine and dried ($Na_2SO_4$). Filtration and solvent removal gave an oil which was subjected to silica gel chromatography to separate the two diastereomers. VIII (61 mg, 25% yield) was obtained as colorless liquid: $R_f$ 0.15 (60% EtOAc/hexanes); $^1$H-NMR (CDCl$_3$) δ 7.17 (m, 1H), 6.90 (m, 2H), 6.78 (m, 1H), 5.84 (m, 2H), 5.35 (m, 2H), 5.00 (septet, J=6.4 Hz, 1H), 4.55 (m, 1H), 4.40 (m, 1H), 3.80–4.15 (broad m, 5H), 1.90–2.65 (broad m, 8H), 1.75 (m, 2H), 1.45 (m, 2H), 1.21 (d, J=7.4 Hz, 6H); $^{13}$C-NMR (CDCl$_3$) δ 173.08, 159.19, 134.90, 132.69, 130.68, 130.57, 130.26, 128.07, 121.35, 115.09, 113.04, 82.21, 75.45, 72.62, 71.83, 70.12, 67.94, 50.84, 34.36, 25.78, 24.55, 22.70, 21.89, 21.80; HRMS m/z calculated for $C_{24}H_{33}O_6ClNa$ (M+Na$^+$) 475.185884, found 475.18588.

EXAMPLE 6

Synthesis of IX

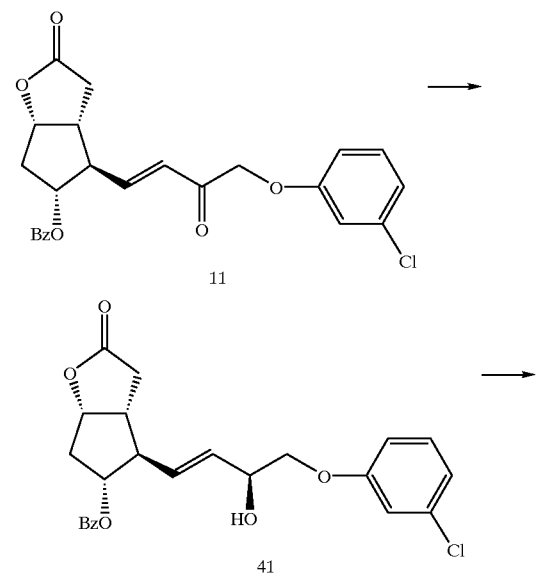

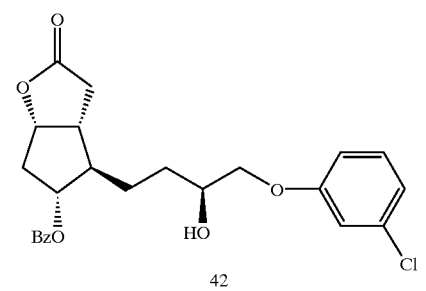

42

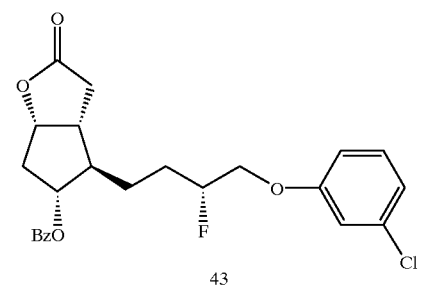

43

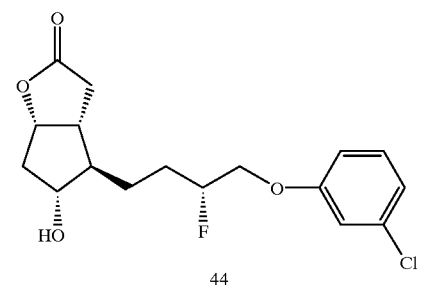

44

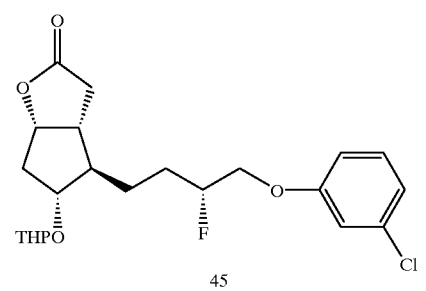

45

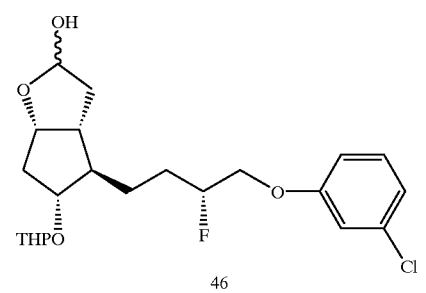

46

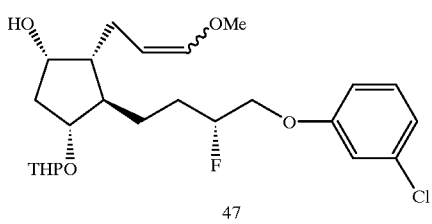

47

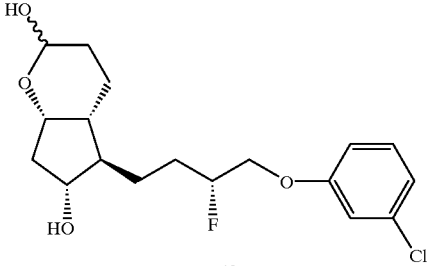

48

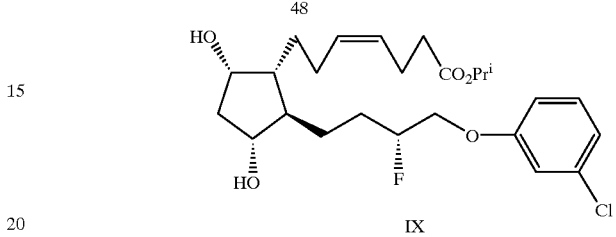

IX (4Z)-(9S,11R,15R)-16-(3-Chlorophenoxy)-9,11-dihydroxy-15-fluoro-17,18,19,20-tetranor-4-prostenoic acid isopropyl ester (IX)

Ketone reduction of 11 with (+)-B-chlorodiisopinocampheylborane in THF at 0° C. affords C-15 β-hydroxy isomer 41 after chromatographic purification. Olefin reduction using Pd/C under a hydrogen atmosphere in ethyl acetate solvent provides alcohol 42, which is fluorinated using DAST to yield α-fluoride 43. Debenzoylation with potassium carbonate in methanol gives alcohol 44, which is treated with 3,4-dihydro-2H-pyran in methylene chloride in the presence of TsOH to afford THP ether 45. Reduction of 45 to lactol 46 is effected with DIBAL-H at −78° C. in toluene, and Wittig condensation of 46 with with $Ph_3P^+CH_2OMe\ Cl^-$ in the the presence of $KOBu^t$ in THF yields enol ether 47. Acidic hydrolysis using TsOH in THF and water gives lactol 48, which is reacted with $Ph_3P^+(CH_2)_3CO_2H\ Br^-$ in the presence of $KOBu^t$ in THF, followed by treatment of an acetone solution of the resulting carboxylic acid with DBU and isopropyl iodide, to afford IX.

The cis-$\Delta^4$ analogs of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between 4.5 to 8.0. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil) cyclodextrin; or other agents known to those skilled in the art. Such co-solvents are typically employed at a level between about 0.01% and about 2% by weight.

Viscosity Age

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight Preferred formulations of cis-$\Delta^4$ prostaglandins of the present invention include the following Examples 8–11:

EXAMPLE 8

| Ingredient | Amount (wt %) |
| --- | --- |
| Compound IV or V | 0.001 |
| Phosphate Buffered Saline | 1.0 |
| Polysorbate 80 | 0.5 |
| Purified water | q.s. to 100% |

EXAMPLE 9

| Ingredient | Amount (wt %) |
| --- | --- |
| Compound IV or V | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 10

| Ingredient | Amount (wt %) |
| --- | --- |
| Compound IV or V | 0.005 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.5 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 11

| Ingredient | Amount (wt %) |
| --- | --- |
| Compound IV or V | 0.01 |
| Phosphate Buffered Saline | 1.0 |
| Hydroxypropyl-β-cyclodextrin | 4.0 |
| Purified water | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma or ocular hypertension in a patient, which comprises administering to the patient a pharmaceutically effective amount of a compound of formula III:

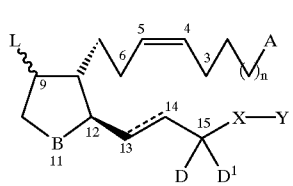

III wherein:
  A=$CO_2R$, $CONR^1R^2$, $CH_2OR^3$, or $CH_2NR^4R^5$; where R=H or cationic salt moiety, or $CO_2R$=ophthalmically acceptable ester moiety; $R^1$, $R^2$=same or different=H or alkyl; $R^3$=H, acyl, or alkyl; $R^4$, $R^5$=same or different=H, acyl, or alkyl, with the proviso that if one of $R^4$, $R^5$=acyl, then the other=H or alkyl;
  n=0 or 2;
  L=$OR^6$ in the α configuration, where $R^6$=H, alkyl, or acyl;

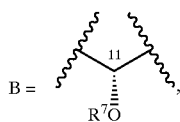

B = where $R^7$=H, alkyl, acyl;

— — — — =single or trans double bond;
D, $D^1$=different=H and $OR^8$, where $R^8$=H, alkyl, acyl;
$X=(CH_2)_m$ or $(CH_2)_mO$, where m=1–6; and
Y=a phenyl ring optionally substituted with alkyl, halo, trihalomethyl, alkoxy, acyl, acyloxy, amino, alkylamino, acylamino, or hydroxy; or
$X-Y=(CH_2)_pY^1$; where p=0–6; and

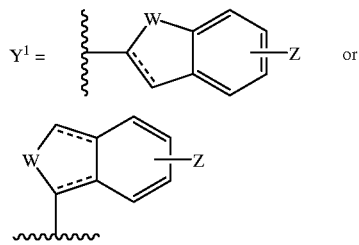

wherein:
$W=CH_2$, O, $S(O)_q$, $NR^9$, $CH_2CH_2$, CH=CH, $CH_2O$, $CH_2S(O)_q$, CH=N, or $CH_2NR^9$; where q=0–2, and $R^9$=H, alkyl, or acyl;
Z=H, alkyl, alkoxy, acyl, acyloxy, halo, trihalomethyl, amino, alkylamino, acylamino, or hydroxy; and
— — — =single or double bond;
with the proviso that if:
$L=OR^6$ in the α configuration, where $R^6$ is as defined above;

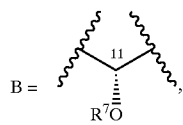

where $R^7$ is as defined above;
— — — =trans double bond;
D, $D^1$=different=H and $OR^8$, where $R^8$ is as defined above; and
$X=CH_2CH_2$ or $CH_2O$; then
Y≠a phenyl ring, optionally substituted with halo.

2. The method of claim 1, wherein the compound is administered topically.

3. The method of claim 2, wherein the compound is administered as a solution, suspension or emulsion.

4. The method of claim 1, wherein:
$A=CO_2R$, where R=H; or $CO_2R$=ophthalmically acceptable ester moiety, where R=alkyl;
n=0;
L=OH in the α configuration;
$R^6$=H;

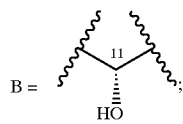

D=OH in the α configuration, and $D^1$=H in the β configuration;
$X=CH_2CH_2$ or $CH_2O$; and
Y=phenyl, optionally substituted with halo or trihalomethyl; or

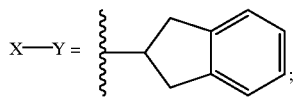

with the proviso that if:
L=OH in the α configuration;

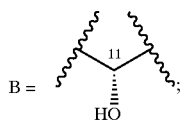

— — — =trans double bond;
D=OH in the α configuration, and $D^1$=H in the β configuration; and
$X=CH_2CH_2$ or $CH_2O$; then
Y≠a phenyl ring, optionally substituted with halo.

5. The method of claim 2, wherein the concentration of the compound is between about 0.00003 to about 0.5 weight percent.

6. The method of claim 5, wherein the concentration of the compound is between about 0.0005 to about 0.03 weight percent.

7. The method of claim 6, wherein the concentration of the compound is between about 0.001 to about 0.01 weight percent.

8. The method of claim 5, wherein the compound is:

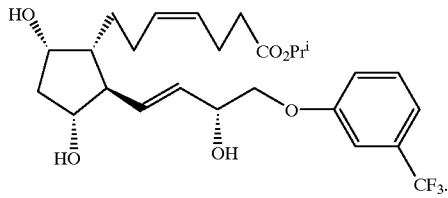

9. The method of claim 5, wherein the compound is:

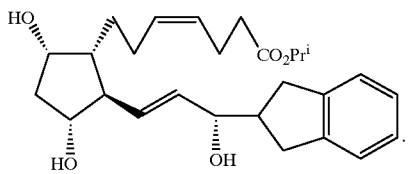

10. A compound of formula III:

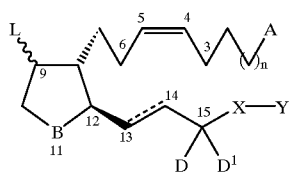

III wherein:
$A=CO_2R$, $CONR^1R^2$, $CH_2OR^3$, or $CH_2NR^4R^5$; where R=H or a cationic salt moiety or $CO_2R$ forms a pharmaceutically acceptable ester moiety; $R^1$, $R^2$=same or different=H or alkyl; $R^3$=H, acyl, or alkyl; $R^4$, $R^5$=same or different=H, acyl, or alkyl; with the proviso that if one of $R^4$, $R^5$=acyl, then the other=H or alkyl;

n=0 or 2;

L=$OR^6$ in the α configuration, where $R^6$=H, alkyl, or acyl;

B = 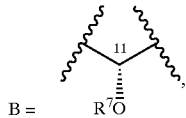

where $R^7$=H, alkyl, acyl;

— — —=single or trans double bond;

D, $D^3$=different=H and $OR^8$, where $R^8$=H, alkyl, acyl;

X–Y=$(CH_2)_p Y^1$; where p=0–6; and $Y^1$ = 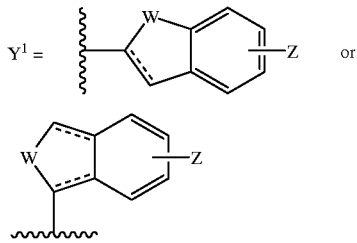 or wherein:

W=$CH_2$, O, $S(O)_q$, $NR^9$, $CH_2CH_2$, CH=CH, $CH_2O$, $CH_2S(O)_q$, CH=N, or $CH_2NR^9$; where q=0–2, and $R^9$=H, alkyl, or acyl;

Z=H, alkyl, alkoxy, acyl, acyloxy, halo, trihalomethyl, amino, alkylamino, acylamino, or hydroxy; and — — —=single or double bond.

11. The compound of claim 10, wherein:

A=$CO_2R$, where R=H; or $CO_2R$=pharmaceutically acceptable ester moiety, where R=or alkyl;

n=0;

L=OH in the α configuration;

B = 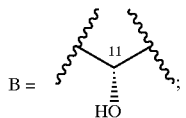

D=OH in the α configuration, and $D^1$=H in the β configuration;

X—Y = 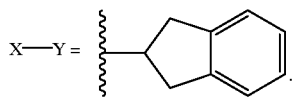

12. The compound of claim 11, having the formula:

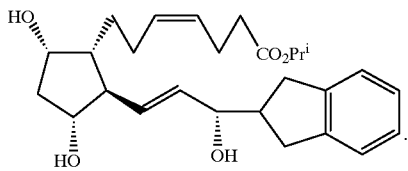

13. A topical ophthalmic composition for the treatment of glaucoma and ocular hypertension, comprising a compound of formula III:

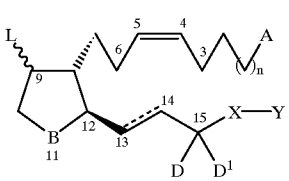

III wherein:

A=$CO_2R$, $CONR^1R^2$, $CH_2OR^3$, or $CH_2NR^4R^5$; where R=H or cationic salt moiety, or $CO_2R$=ophthalmically acceptable ester moiety; $R^1$, $R^2$=same or different=H or alkyl; $R^3$=H, acyl, or alkyl; $R^4$, $R^5$=same or different=H, acyl, or alkyl, with the proviso that if one of $R^4$, $R^5$=acyl, then the other=H or alkyl;

n=0 or 2;

L=$OR^6$ in the α configuration, where $R^6$=H, alkyl, or acyl;

B = 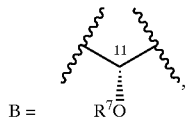

where $R^7$=H, alkyl, acyl;

— — —=single or trans double bond;

D, $D^1$=different=H and $OR^8$, where $R^8$=H, alkyl, acyl;

X=$(CH_2)_m$ or $(CH_2)_mO$, where m=1–6; and

Y=a phenyl ring optionally substituted with alkyl, halo, trihalomethyl, alkoxy, acyl, acyloxy, amino, alkylamino, acylamino, or hydroxy; or X–Y=$(CH_2)_p Y^1$; where p=0–6; and $Y^1$ = 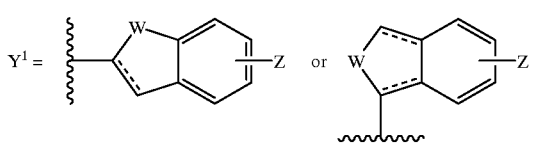

wherein:

W=$CH_2$, O, $S(O)_q$, $NR^9$, $CH_2CH_2$, CH=CH, $CH_2O$, $CH_2S(O)_q$, CH=N, or $CH_2NR^9$; where q=0–2, and $R^9$=H, alkyl, or acyl;

Z=H, alkyl, alkoxy, acyl, acyloxy, halo, trihalomethyl, amino, alkylamino, acylamino, or hydroxy; and — — —=single or double bond;

and an ophthalmically acceptable vehicle therefor;

with the proviso that if:

L=$OR^6$ in the α configuration, where $R^6$ is as defined above;

B = 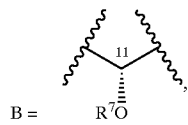, where $R^7$ is as defined above;
— — —=trans double bond;
D, $D^1$=different=H and $OR^8$, where $R^8$ is as defined above; and
X=$CH_2CH_2$ or $CH_2O$; then
Y≠a phenyl ring, optionally substituted with halo.

14. The composition of claim 13, wherein:
A=$CO_2R$, where R=H; or $CO_2R$=ophthalmically acceptable ester moiety, where R=or alkyl;
n=0;
L=OH in the α configuration;

B = 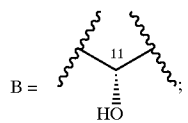;

D=OH in the α configuration, and $D^1$=H in the β configuration;
X=$CH_2CH_2$ or $CH_2O$; and
Y=phenyl, optionally substituted with halo or trihalomethyl; or X—Y = 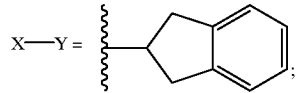;

with the proviso that if:
L=OH in the α configuration;

B = 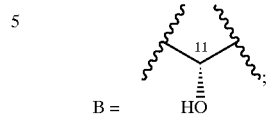;

— — —=trans double bond;
D=OH in the α configuration, and $D^1$=H in the β configuration; and
X=$CH_2CH_2$ or $CH_2O$; then
Y≠a phenyl ring, optionally substituted with halo.

15. The composition of claim 14, wherein the compound is:

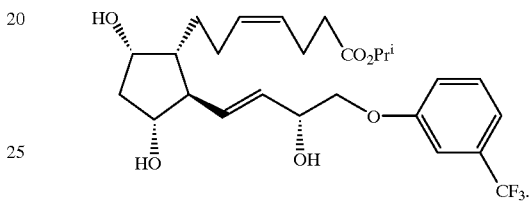

16. The composition of claim 14, wherein the compound is:

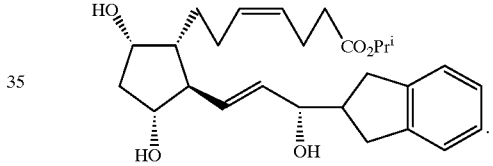

* * * * *